(12) United States Patent
McAnena

(10) Patent No.: US 11,850,041 B2
(45) Date of Patent: Dec. 26, 2023

(54) BED EXIT MONITORING

(71) Applicant: Response Times Limited, Cheshire (GB)

(72) Inventor: Steven McAnena, Blackpool (GB)

(73) Assignee: RESPONSE TIMES LIMITED, Cheshire (GB)

( * ) Notice: Subject to any disclaimer, the term of this patent is extended or adjusted under 35 U.S.C. 154(b) by 219 days.

(21) Appl. No.: 17/423,666

(22) PCT Filed: Jan. 15, 2020

(86) PCT No.: PCT/GB2020/050077
§ 371 (c)(1),
(2) Date: Jul. 16, 2021

(87) PCT Pub. No.: WO2020/148533
PCT Pub. Date: Jul. 23, 2020

(65) Prior Publication Data
US 2022/0071512 A1 Mar. 10, 2022

(30) Foreign Application Priority Data
Jan. 16, 2019 (GB) .................................... 1900581

(51) Int. Cl.
*A61B 5/11* (2006.01)
*A61B 5/00* (2006.01)
*A61B 5/01* (2006.01)

(52) U.S. Cl.
CPC .......... *A61B 5/1115* (2013.01); *A61B 5/0046* (2013.01); *A61B 5/0077* (2013.01);
(Continued)

(58) Field of Classification Search
CPC ........................... A61G 7/012; A61G 2205/60
(Continued)

(56) References Cited

U.S. PATENT DOCUMENTS 4,196,425 A 4/1980 Weekly et al.
9,972,187 B1 5/2018 Srinivasan et al.
(Continued)

FOREIGN PATENT DOCUMENTS

| CN | 107316439 A | 11/2017 |
|---|---|---|
| EP | 2460469 A1 | 6/2012 |
| WO | 2012/040554 A3 | 3/2012 |

OTHER PUBLICATIONS

International Search Report from corresponding international patent application No. PCT/GB2020/050077, dated May 25, 2020, 3 pages.
(Continued)

*Primary Examiner* — Fabricio R Murillo Garcia
(74) *Attorney, Agent, or Firm* — George N. Chaclas; Anthony A. Kassas; DAY PITNEY LLP

(57) ABSTRACT

A bed exit detection device (100) according to an embodiment of the present invention is mounted to a privacy rail (11) provided in the vicinity of a bed (10) to be monitored. The device (100) comprises a thermographic sensor (130) and a range sensor (40). The thermographic sensor comprises an array of sensing elements operable to generate an output value matrix from the output signals of each individual sensing element. The device (100) is also provided with a processing unit (150) operable to process the output value matrix of the thermographic sensor (130) and the distance output by the range sensor (140) so as to determine the position of a bed occupant and thereby (10) determine the likelihood of a bed exit event.

24 Claims, 8 Drawing Sheets

(52) U.S. Cl.
CPC ............ *A61B 5/015* (2013.01); *A61B 5/6889* (2013.01); *A61B 5/6891* (2013.01); *A61B 5/746* (2013.01); *A61B 5/747* (2013.01); *A61B 2562/0271* (2013.01); *A61B 2562/046* (2013.01)

(58) Field of Classification Search
USPC ...................................................... 340/573.4
See application file for complete search history.

(56) References Cited

U.S. PATENT DOCUMENTS

| | | |
|---|---|---|
| 2008/0169931 A1 | 7/2008 | Gentry et al. |
| 2009/0119843 A1* | 5/2009 | Rodgers ................. G16Z 99/00 |
| | | 705/3 |
| 2009/0278934 A1* | 11/2009 | Ecker ..................... G06V 40/25 |
| | | 348/152 |
| 2012/0075464 A1* | 3/2012 | Derenne ............. A61B 5/0036 |
| | | 600/595 |
| 2015/0025327 A1 | 1/2015 | Young et al. |
| 2015/0112151 A1 | 4/2015 | Muhsin et al. |
| 2015/0323388 A1 | 11/2015 | Kostic et al. |
| 2015/0379851 A1 | 12/2015 | Diels |
| 2017/0103524 A1* | 4/2017 | Franz .................... G06T 7/0012 |
| 2017/0156638 A1 | 6/2017 | Ribble et al. |
| 2017/0360357 A1 | 12/2017 | Larson et al. |
| 2019/0156645 A1* | 5/2019 | Bolduc .............. G08B 21/0461 |

OTHER PUBLICATIONS

Written Opinion from corresponding international patent application No. PCT/GB2020/050077, dated May 25, 2020, 7 pages.
Search Report from corresponding Great Britain patent application No. 1900581.8, dated Jun. 27, 2019, 4 pages.

\* cited by examiner

BED EXIT MONITORING

CROSS-REFERENCE TO RELATED APPLICATIONS

This application is a U.S. national stage application under 35 U.S.C. 371 of co-pending International Application No. PCT/GB2020/050077 filed on Jan. 15, 2020, which in turn claims priority to G.B. Application No. 1900581.8 filed on Jan. 16, 2019, the contents of which are incorporated by reference herein in their entirety for all purposes.

TECHNICAL FIELD OF THE INVENTION

The present invention relates to movement monitoring and in particular to bed exit movement monitoring.

BACKGROUND TO THE INVENTION

With particular respect to elderly patients, falls in hospital or other care environments are a significant cause of further injury or recovery setbacks. In many instances, a fall leads to a serious injury, such as a hip fracture. This can significantly and permanently reduce mobility and independence increasing the risk of other health complications up to and including premature death.

There is therefore much activity directed to monitoring patient movement in an attempt to detect bed exit events. If a suitable alarm can be raised, care staff such as nurses can be altered to a bed exit attempt by a patient. A swift response by the relevant staff may help to alleviate or prevent a fall resulting from the attempted bed exit.

Various bed exit detection systems are known. Known systems include those relying on pressure-sensitive mats or load cells integrated into the patient's bed. Such systems are not ideal as it can be difficult to distinguish between activities indicative of a bed exit attempt and other benign patient movement using such sensors. Additionally, it can be relatively costly or difficult to retrofit such sensors to existing beds.

Other bed exit detection systems rely on affixing sensors, such as accelerometers, to patients. Once again, it can be difficult to distinguish between activities indicative of a bed exit attempt and other benign patient movement using such sensors. Furthermore, such sensors may be uncomfortable for a patient to wear and/or may be susceptible to being removed by a patient or otherwise damaged by a patient.

Another type of bed exit detection system relies on the provision of infrared emitters paired with associated infrared detectors. Such systems may involve the emission of a beam from each emitter, the beam detected by the associated detector. By arranging the emitters and detectors in position along the side of a bed, a bed exit attempt can be inferred when the beam is blocked. Such systems can be prone to false alarms if the beam is blocked for innocent reasons, such as movements of a visitor or member of staff in the vicinity of the bed or by the rearrangement of bedding or other items near the bed. If the beams are arranged carefully so as to avoid being blocked by simple movements or bedding or the like, it may well be that they are not broken by patient movement until a bed exit attempt is complete or nearly complete. As such, any alarm provided may provide insufficient time for a staff response to prevent a fall.

It is therefore an object of the present invention to provide a bed exit monitoring system and method that at least partially overcomes or alleviates the above problems.

SUMMARY OF THE INVENTION

According to a first aspect of the present invention there is provided a bed exit detection device comprising: a thermographic sensor comprising an array of sensing elements, each operable to output signals corresponding to the temperature of a corresponding segment within the field of view of the thermographic sensor and to generate an output value matrix from the output signals of each individual sensing element; a range sensor operable to determine and output the distance between the range sensor and an object; and a processing unit operable to process the output value matrix of the thermographic sensor and the distance output by the range sensor so as to determine the position of a bed occupant and thereby determine the likelihood of a bed exit event.

According to a second aspect of the present invention there is provided a method of operating a bed exit detection device comprising: a thermographic sensor of the type comprising an array of sensing elements, each operable to output signals corresponding to the temperature of a corresponding segment within the field of view of the thermographic sensor and to generate an output value matrix from the output signals of each individual sensing element; and a range sensor operable to determine and output the distance between the range sensor and an object, the method comprising the steps of: processing the output value matrix of the thermographic sensor and the distance output by the range sensor so as to determine the position of a bed occupant and thereby determine the likelihood of a bed exit event.

As each sensing element is operable to output a signal indicative of the temperature of a corresponding segment within the field of view of the thermographic sensor, the output value matrix can provide a map of the temperature of different segments within the field of view of the thermographic sensor. Accordingly, and since the temperature of segments aligned with a bed occupant differs from other segments, the present invention thus provides for ready detection of the position of a bed occupant. Based on the position of the occupant within the bed, the likelihood of a bed exit event can be determined, whether as an event in progress or as a likelihood that an attempt at a bed exit will be made imminently. In addition, the range sensor can be used to resolve ambiguities in determining the position of the bed occupant. The sensors of the present invention are relatively resistant to being blocked by other activity in the vicinity of the bed or to the generation of false alarms in response to benign movement. The thermographic sensor need not be attached directly to a bed occupant to operate. Additionally, the sensors also allow for likely imminent bed exit attempts to be detected, allowing for these to be averted by prompt intervention. The provision of the bracket facilitates ready mounting of the device in a suitable position to monitor a bed.

The method of the second aspect of the present invention may be applied to a bed exit device according to the first aspect of the present invention.

The sensors may be aligned with a bed to be monitored. In particular, the field of view of the thermographic sensor and/or the range sensor may be aligned with the bed. This alignment may be achieved by use of a suitable mounting bracket. The range sensor may be operable only to detect objects within a predetermined maximum distance of the range sensor. The predetermined maximum distance may be less than the length of the bed. In a preferred embodiment, the predetermined maximum distance is substantially coincidental with the mid-point of the monitored bed.

The range sensor may be a sensor of the type operable to output a ranging beam and detect reflections of the ranging beam. By analysing the time of flight of the detected reflections of the ranging beam, the distance to an object may be determined. A predetermined maximum detection distance can be implemented by ignoring detected reflections with a time of flight indicative of reflection from beyond the predetermined maximum distance. The ranging beam may be an ultrasonic beam or an electromagnetic beam, as desired or required. If the ranging beam is an electromagnetic beam, it may be a visible or infrared beam.

The device may be mounted in an elevated position with respect to the bed to be monitored. The elevated position advantageously reduces the likelihood of objects blocking each sensor. In addition, the sensors are less likely to be damaged by bed occupants moving in the bed.

The device may comprise a bracket. The bracket may facilitate mounting the device to a privacy rail in the vicinity of the bed. In such embodiments, the bracket may define a slot adapted to engage with the privacy rail.

In other embodiments, the bracket may facilitate mounting the device to a wall or ceiling. In further embodiments, the device may be provided with a clamping arrangement adapted so as to secure the device to the bed.

The device may comprise an illumination unit. The illumination unit may be provided alongside the thermographic sensor and the range sensor. The illumination unit may provide illumination to the bed. The illumination may be steady illumination or varying illumination. In particular, the illumination unit may provide background or ambient lighting to the bed. Such illumination can improve the environment for the bed occupant and may further improve the bed occupant's acceptance of the device. This can reduce the likelihood that the device is tampered with.

The device may comprise visual output means. The visual output means may comprise one or more indicator lamps. The visual output means may additionally or alternatively comprise a display unit. The display unit may comprise a liquid crystal (LCD), light emitting diode (LED) or organic light emitting diode (OLED) display, as required or as desired.

The display unit may be operable to output an image representative of the output value matrix. The display unit may additionally or alternatively be operable to output any one or more of the following items of information: device power status; range sensor information, including but not limited to predetermined maximum distance; thermographic sensor information, including but not limited to thermographic sensor sensitivity; device identity or location information, including but not limited to device identity, MAC address, IP address or bed identity.

The device may be provided with user actuable input means. The input means may comprise one or more push switches. The input means may be operable to enable any one or more of the following: vary thermographic sensor sensitivity; vary range sensor maximum distance; reset device; toggle display mode; start/stop monitoring; toggle illumination unit activation or the like. Additionally or alternatively, the device may be provided with a power on/off switch.

The input means may be provided alongside the sensors. Alternatively, the input means may be provided in an interface unit separated from the sensors. The interface unit may be placed in a convenient location for use when the sensors are mounted in an elevated or inaccessible position. Signals may be communicated between the sensors and the interface unit via any suitable wired connection or a wireless connection.

The device may be provided with a suitable power source. The power source may be a mains connection and/or an internal battery. The battery may be a rechargeable battery. Where there is an interface unit provided remote from the sensors, the power source may be integrated into the interface unit. The interface unit may also facilitate additional external power and or data connections. This can therefore allow a carer to interact with the device at the bedside and can also afford the bed occupant the convenience of powering or providing data connections for their personal electronic equipment.

The device may be provided with a communication unit. The communication unit may be operable to transmit data to or receive data from one or more external devices. The communication unit may be operable to transmit data over any suitable wired or wireless link. In preferred embodiments, the link is a wireless link. The wireless link may operate in accordance with any suitable protocol including but not limited to: WiFi, Bluetooth, Zigbee or the like.

In particular, the communication unit may be operable to transmit status signals indicative of the current operating status of the device and or the current sensor output. Additionally or alternatively, the communication unit may be operable to transmit an alarm signal when a bed exit attempt is detected.

The processing unit may be operable to output an alarm signal in response to a detected bed exit event. In response to the alarm signal, a visible alarm may be output using the display and/or indicator lamps. Additionally or alternatively, an audible alarm may be output by an integrated loudspeaker.

The one or more remote devices may comprise a control console and/or one or more carer terminals. The or each external device may be operable to output visible or audible status information or alarms, as appropriate. Alarms may include information identifying the device which generated the alarm signal and/or the nature of the alarm.

The device may be operable in combination with one or more external sensors. The one or more external sensors may communicate to the device via the interface unit. In one embodiment, an external sensor may be a pressure sensor incorporated into a chair. Typically, the chair is adjacent to the bed. The pressure sensor may be in communication with the device via the communication unit and/or the interface unit. In such embodiments, the device may be additionally operable to detect that a bedside chair is occupied. Additionally or alternatively, the device may be operable to monitor occupation of the chair and/or chair exit attempts.

The thermographic sensor array may comprise any suitable number of sensing elements. In preferred embodiments, the number of sensing elements is sufficient to determine the position of a bed occupant with relation to the bed but not so many sensing elements as to require excessive processing power. This may be readily achieved with a relatively low definition thermographic sensor. Such a sensor may comprise, say, 64 sensing elements arranged in an 8 by 8 square array. The output value matrix may correspond to the sensing element array.

The processing unit may be operable to determine that the output values of one or more sensing elements within the output value matrix indicate that corresponding segments of the bed contain the occupant by reference. In such embodiments, the processing unit may be operable to determine whether each output value in the output value matrix is within a characteristic range. If so, the processing unit may determine that the segment of the bed corresponding to each such sensing element contains an occupant. Such segments can be identified as occupied segments. The processing unit can thus determine the position of a bed occupant by reference to the occupied segments.

The upper threshold of the characteristic range may be pre-set. In particular, the upper threshold of the range may be pre-set at a level indicative of a temperature greater than possible body temperature of a human. This can prevent false positives caused by other heat sources for instance hot drinks or the like.

The lower threshold of the characteristic range may be pre-set. Additionally or alternatively, the lower threshold of the characteristic range may be varied in response to the overall output of the thermographic sensor and/or to the sensitivity setting of the characteristic sensor. This can enable the device to adapt to variations in ambient temperature and body temperature of the bed occupant over time. In some embodiments, the lower threshold of the characteristic range may be calculated from the sum of the lowest output value and the sensitivity setting.

In this context, the lower threshold of the characteristic range may be varied in response to the sensing element of the thermographic sensor with the lowest output value. the lowest value may be the lowest value in each output value matrix or may be the lowest value in any output value matrix captured during a particular period.

The sensitivity setting of the thermographic sensor may define an offset value. The offset value may vary the lower threshold of the characteristic range from a pre-set value or a value related to the output value matrix of the thermographic sensor. The sensitivity setting may be varied in response to the user actuable inputs. In some embodiments, the sensitivity setting may be selected by outputting an image representative of the output value matrix for a bed to be monitored containing an occupant; reducing the thermographic sensor sensitivity until substantially no features are detectable in the representative image; and then increasing the sensor sensitivity until features corresponding to the position of the occupant on the bed are visible in the representative image. In some embodiments, the sensitivity setting may be adjusted in response to calculations performed by the processing unit. These calculations may involve machine learning.

The processing unit may be operable to divide the output value matrix into a plurality of zones. In one example the output value matrix may be divided into four zones. The zones may correspond to different areas of the bed to be monitored or the vicinity thereof. Each zone may be defined by reference to a subset of sensing elements of the thermographic sensor or of segments within the output value matrix. The zone boundaries may be fixed or may be varied, as required or as appropriate. Where zone boundaries are variable, the zone boundaries may be set after calibration.

The processing unit may be operable to determine whether each zone is occupied by determining whether the number of occupied segments within a zone exceeds a zone threshold value. The zone threshold value may be equal for each zone or may vary for different zones. The processing unit can thus determine the position of a bed occupant by reference to the occupied segments. This requires less processing power than processing the location of occupied segments independently.

The processing unit may be operable to determine the position of a bed occupant by reference to the occupied zones. This position can thus indicate the existence of a bed exit event or imminent bed exit event. For instance, if only the left zone or the right zone is occupied, the processing unit can determine that a bed exit attempt to the respective side of the bed is in progress or imminent.

The processing unit may be operable to monitor the overall proportion of occupied segments. In response to the overall proportion of occupied segments, the processing unit may determine that the bed is unoccupied and/or the view of the thermographic sensor is blocked.

The processing unit may additionally process the output of the range sensor in determining whether the bed is occupied at all or whether the sensor is blocked. In particular, the processing unit may be operable to vary the zone threshold value for one or more zones in response to the range sensor. For instance, if the output of the range sensor indicates that an object is close to the device, the processing unit may determine that a particular occupied zone or occupied segment configuration is indicative of a blocked sensor. Alternatively, if the output of the range sensor indicates that no object is close to the device, the processing unit may determine that the bed is unoccupied.

The output value matrix may comprise a left zone comprising one or more columns of segments at the edge of the output value matrix. This zone thereby corresponds to the left edge of the bed to be monitored. The zone threshold value for the left zone may be, say, 12.5%, 18.75% or 25% of the segments within the zone.

The output value matrix may comprise a right zone comprising one or more columns of segments at the edge of the output value matrix. This zone thereby corresponds to the right edge of the bed to be monitored. The zone threshold value for the right zone may be, say, 12.5%, 18.75% or 25% of the segments within the zone.

The output value matrix may comprise a centre zone between the left and right zones. This zone thereby corresponds substantially to the bed to be monitored, as viewed from the device. The zone threshold value for the centre zone may be, say, 15% of the segments s within the zone.

In some embodiments, the centre zone may be split into a main centre zone and a top zone. The main centre zone may comprise the lower and intermediate portion of segment columns between the left and right zones. As such, the main centre zone may correspond substantially to the centre and foot end of the bed to be monitored. The top zone may comprise the upper portion of segment columns between the left and right zones. This zone thereby corresponds to the head end of the bed to be monitored. The zone threshold value for the top main zone may be, say, 1% of the segments s within the zone.

In some embodiments, the output value matrix may comprise a disabled zone. The output of segments in the disabled zone may be excluded from processing. This exclusion would prevent incorrect inferences being drawn from segment outputs in the disabled zone. Typically, such outputs should be excluded because the imaged areas corresponding to the disabled zone fall outside the bed area. Additionally, or alternatively, the disabled zone may correspond to areas that are not relevant for bed exit detection or may provoke processing errors. The disabled zone could thereby be utilised to exclude from processing other local sources of heat such as radiators, medical equipment or the like.

In one embodiment, the disabled zone may comprise an upper portion of segment columns. The vertical extent of the disabled zone may vary across the segment columns.

According to a third aspect of the present invention there is provided a bed exit monitoring system for monitoring multiple beds, the system comprising: one or more bed exit detection devices according to the first aspect of the present invention and/or operable according to the method of the second aspect of the invention, provided for each monitored bed; and a control console in communication with each bed exit device and operable to output a status indication in response to signals received from each device.

The system of the third aspect of the present invention may incorporate any or all features of the first two aspects of the present invention as desired or as necessary.

The control console may comprise a display unit. The control console may additionally or alternatively comprise an audio output and/or a vibratory output means. The control console may comprise user input means. The user input means may comprise any one or more of: a touch sensitive screen, key pad or pointing device. Typically the control console may comprise a tablet computer, laptop computer or desktop computer.

The system may comprise one or more carer terminals in communication with the control console. Each carer terminal may comprise a display unit. Each carer terminal may additionally or alternatively comprise an audio output and/or a vibratory output means. Each carer terminal may comprise user input means. The user input means may comprise any one or more of: a touch sensitive screen, key pad or pointing device. Typically, each carer terminal may comprise a smartphone, tablet computer or other portable unit suitable for being carried by a carer.

The control console may be operable to output status information relating to each bed exit detection device. Each bed exit detection device may be operable to generate and communicate an alarm signal in response to a detected bed exit event. In response to the alarm signal, the control console may be operable to output an alarm.

The alarm may include information identifying the bed exit detection device that generated the alarm signal.

The control console may be operable to communicate the alarm signal to each carer terminal. In response, each carer terminal may be operable to output an alarm. This can alert a responsible carer to a bed exit event. The alarm may include information identifying the bed exit detection device that generated the alarm signal. In response to an alarm, a carer terminal can be operable to generate an acknowledgement signal. The action signal may be generated in response to activation of user input means by a carer. The acknowledgement signal may comprise an indication of the identity of the carer terminal. The acknowledgement signal may indicate that a carer has noted the alarm and is going to check the identified bed. This may allow a bed exit event to be resolved before the bed occupant is injured. The control console may be operable to output information relating to any acknowledgement signals received.

Communications between the bed exit detection devices, control console and/or carer terminals may utilise any suitable wired or wireless link. In preferred embodiments, the link is a wireless link. The wireless link may operate in accordance with any suitable protocol including but not limited to: WiFi, Bluetooth, Zigbee or the like. Communications between the bed exit detection devices, control console and/or carer terminals may be direct or may be routed via a communication hub.

The control console may be in communication with a remote server. The remote server may be operable to maintain an archive of status information, alarms and acknowledgements. This can allow for retrospective performance audits.

According to a fourth aspect of the present invention, there is provided a method of setting the sensitivity of a bed exit detection device according to the first aspect of the present invention and/or operable according to the method of the second aspect of the invention, the method comprising the steps of: mounting the thermographic sensor such that a bed to be monitored is aligned with the field of view of the thermographic sensor; ensuring an occupant is occupying the bed; outputting an image representative of the output value matrix; reducing the thermographic sensor sensitivity until substantially no features are detectable in the representative image; and then increasing the sensor sensitivity until features corresponding to the position of the occupant on the bed are visible in the representative image.

The method of the fourth aspect of the present invention may incorporate any or all features of the first three aspects of the present invention as desired or as necessary.

According to a fifth aspect of the present invention, there is provided a bed exit detection device comprising: one or more sensors, each sensor output signals for processing by a processing unit so as to determine the position of a bed occupant and thereby determine the likelihood of a bed exit event; and an illumination unit provided alongside the one or more sensors, the illumination unit operable to provide illumination to the bed.

The device of the fifth aspect of the present invention may incorporate any or all features of the first to fourth aspects of the invention as desired or as necessary.

The device of the fifth aspect of the invention can improve the environment for the bed occupant and may further improve the bed occupant's acceptance of the device.

This can reduce the likelihood that the device is tampered with.

DETAILED DESCRIPTION OF THE INVENTION

In order that the invention may be more clearly understood one or more embodiments thereof will now be described, by way of example only, with reference to the accompanying drawings, of which:

Figure 1:
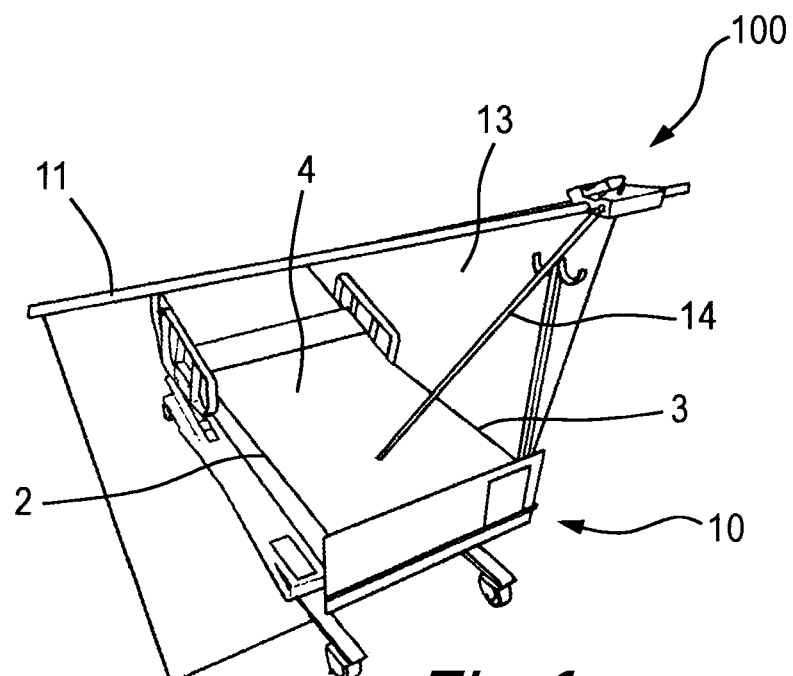
FIG. 1 is a schematic illustration of a bed exit detection device fitted to a bed.

Turning to FIG. 1, a bed exit detection device 100 according to an embodiment of the present invention is mounted to a privacy rail 11 provided in the vicinity of a bed 10 to be monitored. The bed comprises a right edge 2, a left edge 3 and a centre 4. The mounting is achieved by way of a bracket 110, which in this embodiment comprises a slot 111 which in use engages the privacy rail 11. The device 100 is operable to monitor determine the position of a bed occupant 1 (not shown in FIG. 1) and thereby determine the likelihood of a bed exit event. Detecting such events can enable intervention by carers to avert potential negative consequences of bed exit by an elderly or infirm bed occupant 1.

The device 100 comprises a thermographic sensor 130 comprising an array of sensing elements, each sensing element operable to output signals corresponding to the temperature of a corresponding segment within the field of view 13 of the thermographic sensor 130. In use, the thermographic sensor 130 is operable to generate an output value matrix from the output signals of each individual sensing element. The output value matrix thus provides a map of the temperature of different segments within the field of view 13 of the thermographic sensor 130. The field of view 13 of the thermographic sensor 130 is illustrated schematically in FIG. 1. When the device 100 is positioned appropriately, the field of view 13 includes the bed 10 and both edges of the bed 2, 3. Accordingly, the thermographic sensor 130 can thus generate a segment by segment temperature map of bed 10 and an occupant 1 lying anywhere on the bed 10 and/or an occupant sitting anywhere on the bed 10. As such, temperature of each segment in the output value matrix can be used to determine whether each segment is aligned with occupant 1 of the bed 10 or the bed 10 itself.

As is illustrated in FIG. 1, the device 100 is also provided with a range sensor 140 operable to detect the distance between the device 100 and an object such as a bed occupant 1. The range sensor 140 is operable to output a beam 14 and detect reflections of the beam, determining range by calculating the time of flight of the reflected beam. In the embodiment shown in FIG. 1, the range sensor 140 is operable only to detect objects up to a maximum range illustrated by the extent of beam 14 in FIG. 1. This maximum range is in the region of the centre of the bed 10. Additionally, the range sensor 140 is aligned such that it does not detect an occupant 1 lying on the bed 10 but does detect an occupant 1 sitting on the bed 10, within the detection range.

Figure 2:
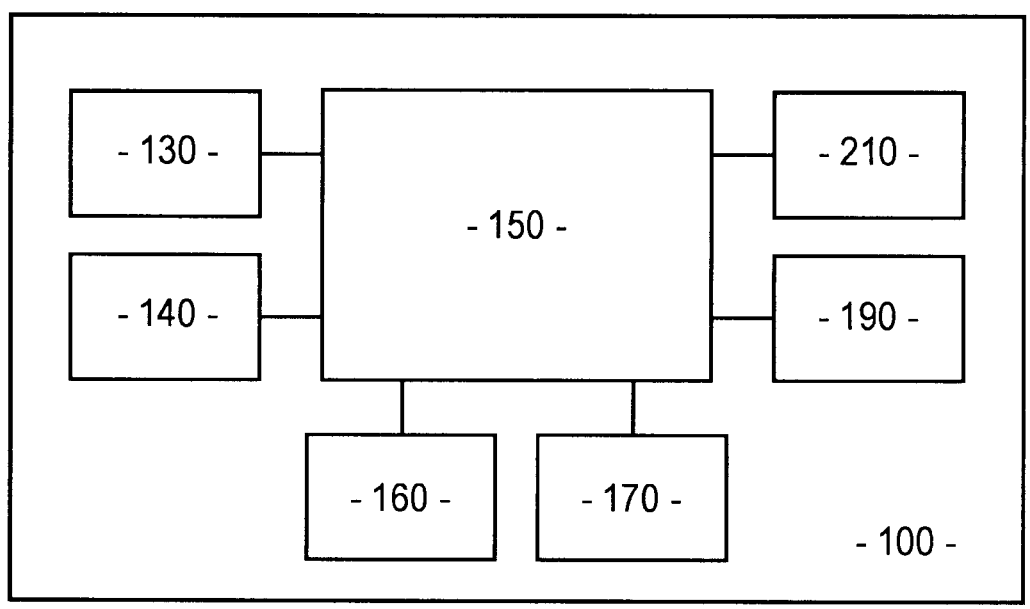
FIG. 2 is a schematic block diagram of the bed exit detection device of FIG. 1.

Turning to FIG. 2, the device 100 comprises a processing unit 150 operable to process the output value matrix and the output of the range sensor 140 so as to determine the position of a bed occupant 1 and thereby determine the likelihood of a bed exit event.

In addition to the sensors 130, 140 and processing unit 150 the embodiment of the device 100 shown in FIG. 2 may additionally comprise a communication unit 160, indicator lamps 170, power source 190 (wired or battery, as required or desired) and interface unit 210. The skilled man will appreciate that the interface unit 210 may be provided adjacent to the other components or separately from the other components, as convenient.

The communication unit 160 is operable to enable signals to be exchanged wirelessly with one or more additional devices in a system 1000 as will be described in more detail below. The communication unit 160 is typically a WiFi transceiver but may be operable in accordance with any other data communication protocol as necessary. This facilitates the embodiment of the device 100 shown in FIG. 2 to communicate via a local WiFi network.

The indicator lamps 170 are operable to display device status. In the illustrated embodiment, the indicator lamps 170 comprise one red, one yellow and one green LED (light emitting diode). The red LED indicates the device 100 has power, the yellow LED indicates data transmission status, and the green LED indicates local WiFi network connectivity. The power source 190 is a wired $5v$ connection. The input means 210 enables operation of the device 100 to be controlled.

Figure 3A:
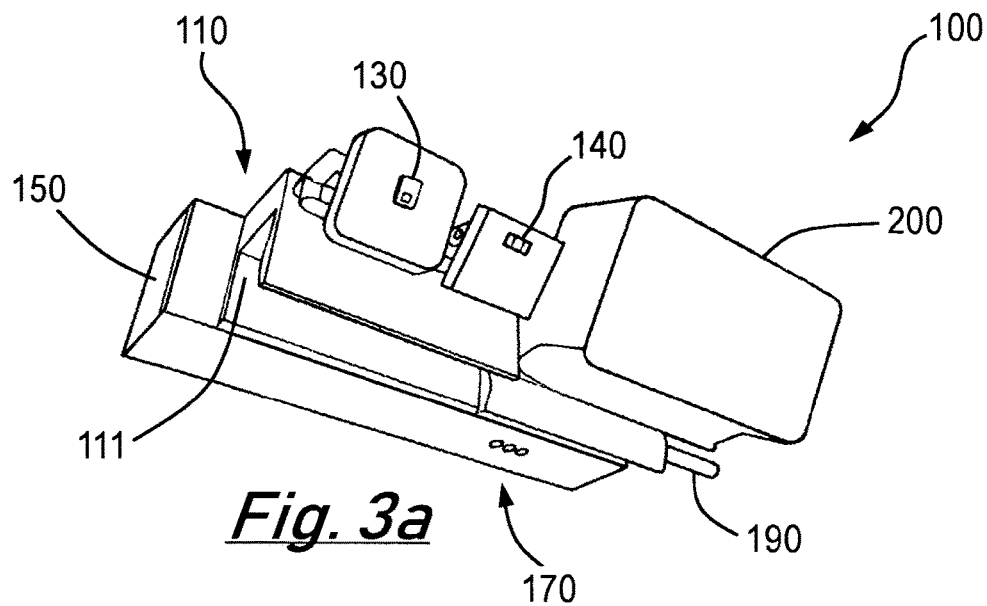
FIG. 3 shows (a) a front and side perspective view of the bed exit detection device of FIG. 1, (b) a side view of the bed exit detection device of FIG. 1; and (c) a perspective view of a user interface unit of the bed exit detection device of FIG. 1.
Figure 3B:
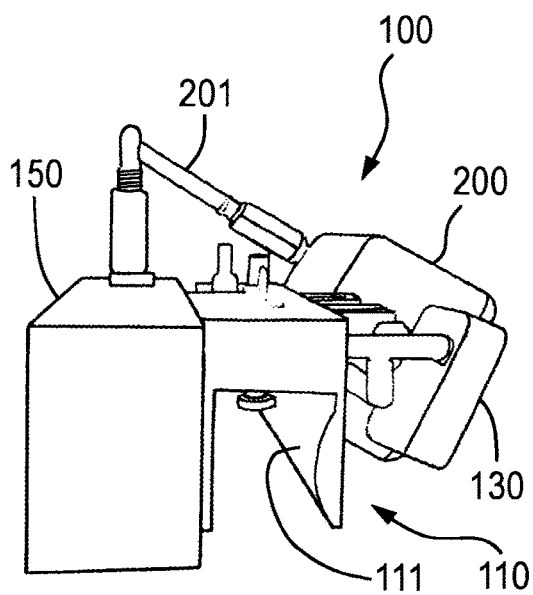
Figure 3C:
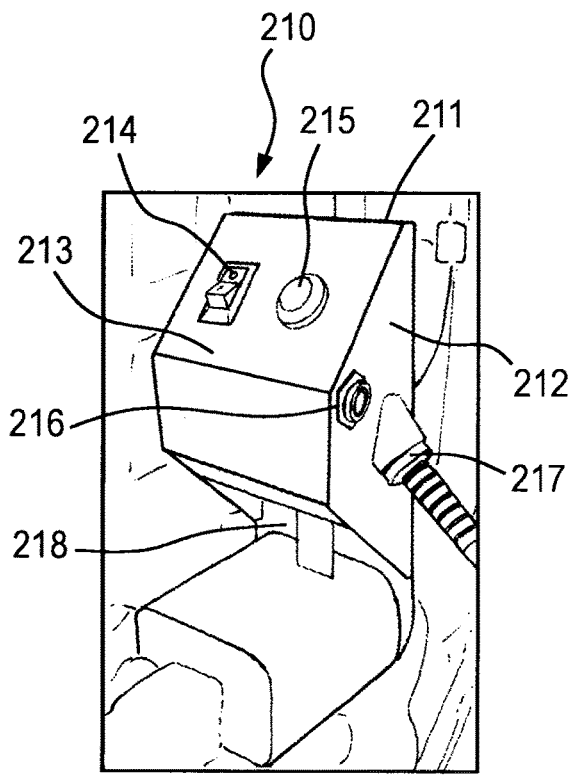

Turning now to FIGS. 3a and 3b, an embodiment of the invention is shown that is designed to be fitted to a bed privacy rail 11 (not shown in FIG. 3a-c). In this example, elongate bracket 110 comprises an inverted U-shaped cross-section slot 111 that engages the privacy rail 11. Processing unit 150 is fitted to one side of the bracket 110. At one end of the processing unit 150, a wired connection provides the power source 190 and relays signals between the device 100 and interface unit 210 (described later). LED indicator lamps 170 are disposed on the housing of the processing unit 150. The thermographic sensor 130 and range sensor 140 are disposed on the opposite side of the bracket 110 from the processing unit 150.

In this embodiment, the device 100 is also fitted with an illumination unit 200. A front face of the illumination unit 200 is fitted with a translucent diffuser. The illumination unit 200 is powered via power lead 201 which connects to the processing unit 150. The illumination unit 200 is disposed on the same side of the bracket 110 as the thermographic sensor 130 and the range sensor 140, such that it is operable to illuminate the bed 10. Typically, the illumination unit 200 may be operated so as to emit diffuse background or ambient illumination of the bed 10.

The thermographic sensor 130 and range sensor 140 are pivotally connected to the bracket 110. This can be achieved by provision of a hinge or other suitable connection. This allows the pitch of each sensor 130, 140 to be independently adjusted to optimise the orientation of each sensor for the position of the device 100 with respect to the bed 10 to be monitored and the local environment. The illumination unit 200 may be similarly mounted and adjusted as necessary.

Additionally, some embodiments of the device 100 may feature a microphone (not shown) configured to output a signal indicative of the local sound pressure to the processing unit 150. The microphone may be a directional microphone and may be mounted next to the thermographic sensor 130. In such embodiments, the processing unit 150 may determine the peak-to-peak sound pressure and use this to output a signal indicative of patient agitation. This can provide further information to carers on the wellbeing of the bed occupant.

Turning now to FIG. 3c, the embodiment shown in FIGS. 3a and 3b also features a user interface unit 210. As the bracket 110 secures the device high on the privacy rail of the bed, the interface unit 210 is provided separately from the device 100 to allow easy access for users. The interface unit 210 comprises a body 212 with a back 211 adapted to facilitate mounting to a bed or wall for easy access. The body 212 has a front face 213 on which is provided a switch 214 and a button 215. The switch 214 controls the operation of illumination unit 200. The button 215 starts and stops bed exit monitoring of the device 100. This allows the monitoring to be paused when the occupant needs to be moved or if the bed needs to be cleaned or bedding changed.

In one side of the body 212, a socket 216 is provided. This allows the device 100 to be connected to an external sensor such as chair pressure sensor (not shown) or other equipment as required or desired. The skilled man will appreciate that additional connection sockets may be provided if required. A wired power connection 217 may provide a power source 190 and wired data connection to the processing unit 150 and sensors 130, 140.

A power socket 218 allows the bed occupant to power or charge personal electronic devices, such as mobile phones, tablets or the like. This further improves the quality of life for the bed occupant as they have convenient access to electrical power.

The skilled man will appreciate that in alternative embodiments, the entire device 100, including both sensors 130, 140, processing unit 150 and interface unit 210 are provided in the same body and are mounted directly to the footboard of the bed. Whilst such embodiments are perhaps more convenient to fit, they are particularly susceptible to tampering with by the bed occupant whether willfully or accidentally.

Figure 4:
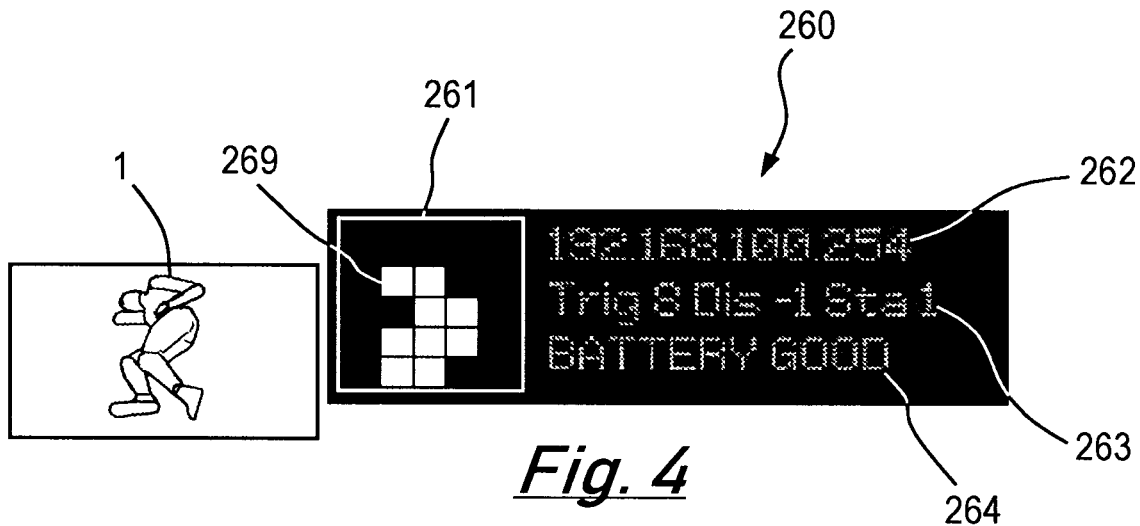
FIG. 4 is schematic illustration of the output of a display unit of a bed exit monitoring device.

In certain embodiments of the invention, a display 260 is provided, either on the device 100 or on interface unit 210. An example of the information provided on such a display 160 is shown in FIG. 4. A portion 261 of the display is operable to display an image 269 indicative of the output value matrix. The displayed image 269 corresponds to the position of a bed occupant 1. In addition to the image 269, the display also provides information as to the device identity/location at 261. A user actuable input means (not shown) can be used to toggle between the IP address, MAC address and device identity number. The display 260 further provides at 263 information on the current sensitivity setting of the thermographic sensor 130, output of the range sensor 140 and status of the device 100. At 264, the display provides information on the status of power supply 190.

Figure 5:
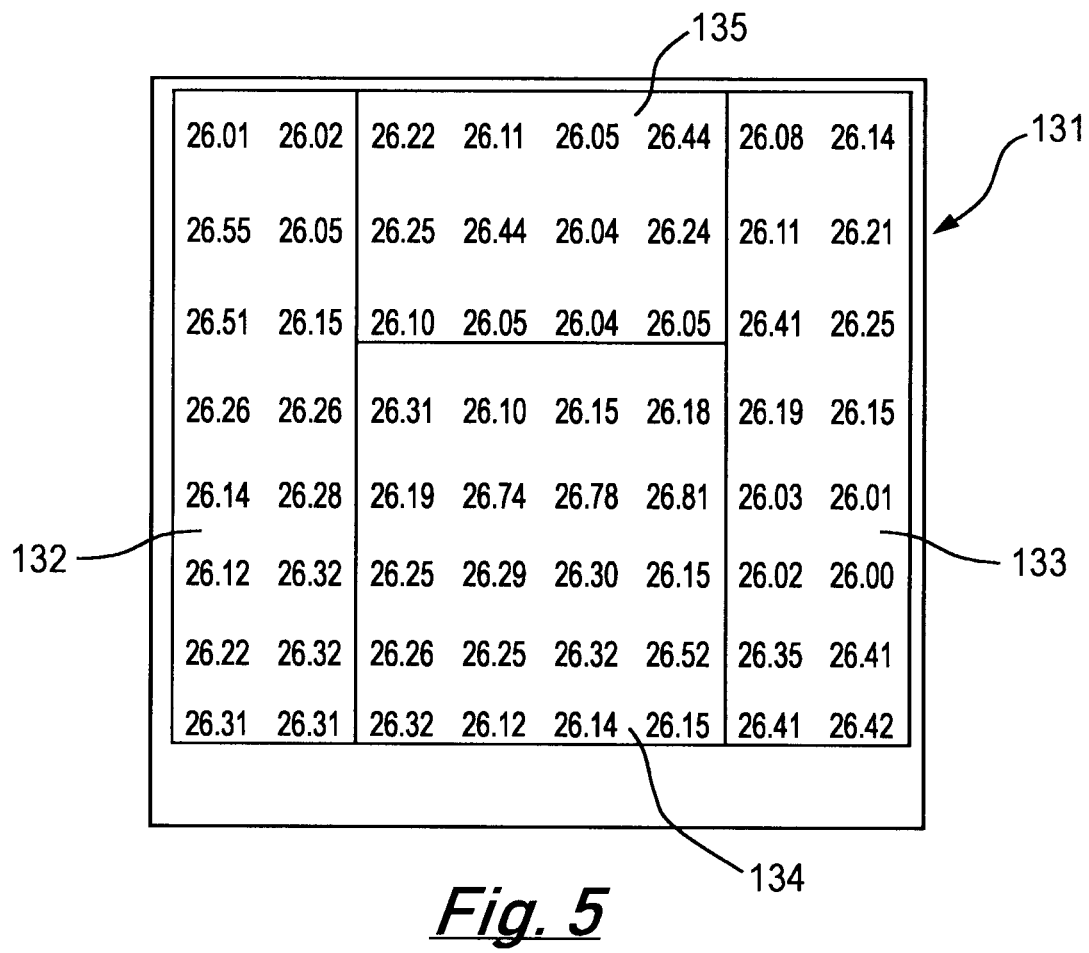
FIG. 5 is a schematic illustration of different detection zones of an output value matrix of thermographic sensor for a bed exit detection device.

FIG. 5 is an illustration of the output value matrix 131. In this example, the output value matrix 131 is an 8 by 8 square array corresponding to an 8×8 square array of sensing elements making up the thermographic sensor 130. The skilled man will appreciate that arrays comprising different numbers of segments and or different configurations of segments may be utilised in the present invention. In any particular implementation the number of segments selected must be sufficient to enable different bed occupant 1 positions to be distinguished. Nevertheless, the skilled man will also appreciate that arrays featuring much larger numbers of segments result in a much greater processing load for the processing unit 150. This can increase the cost and complexity of the device 100 and have an adverse impact on power consumption.

The array shown in FIG. 5 is populated by output signal values for each segment. The output signal values are expressed in a temperature equivalent in degrees Celsius. The processing unit 150 is operable to receive the temperature equivalent values from the thermographic sensor 130 for each segment. The received outputs are subsequently processed to determine whether they fall within a characteristic range. Segment outputs falling within the characteristic range are associated with the bed occupant 1 and thus identified as occupied segments. Segment values falling outside the characteristic range are identified as unoccupied segments.

By considering the occupied segments and the output of the range sensor 140, the processing unit 150 is operable to estimate the position of a bed occupant and hence the likelihood of a bed exit event.

The characteristic range is defined by an upper threshold which is pre-set to a value greater than possible body temperature of a human. The lower threshold of the characteristic range is varied in response to the overall output of the thermographic sensor 130 and the sensitivity setting (an offset value) of the thermographic sensor 130. In a particular example, the lower threshold of the characteristic range is calculated from the sum of the lowest output value in the output value matrix and the sensitivity setting. The lowest output value is typically selected from the present output value matrix. In this context, it has been found that temperature fluctuations, such as transient hot or cold spots can occur intermittently. As such, revising the lower threshold of the characteristic range can minimise the impact of such events on the device 100.

Whilst many readily available thermographic sensors 130 have a sensitivity range from say 0° C. to 80° C., the typical normal bounds of the characteristic range in the present invention will be in the region of 18° C. to 42° C. Whilst the temperature of human skin in a healthy individual is typically in the range 35° C. to 39° C., a wider range of temperature variation can be expected in unhealthy, elderly or infirm individuals.

The outputs, as processed above can be output as the image 169 on the display 160. In order to determine the likely bed occupant position corresponding to each image 169, the processing unit 150 is operable to determine the proportion of occupied segments in a number of different zones.

In order to select a suitable sensitivity setting, a user can adjust the sensitivity whilst the bed 10 is occupied and whilst observing image 169. Firstly, the user reduces the sensitivity setting to a value where the image 169 contains substantially no occupied segments. Subsequently, the user increases the sensitivity setting until features corresponding to the position of the occupant 1 on the bed 10 are visible in image 169. The sensitivity may be set wirelessly using a control console 1200 or carer terminal 1300, which are described below, or any other suitable device, such as a laptop. Additionally or alternatively, the processing unit 150 may be operable to automatically adjust the sensitivity through analysis of the readings of the output value matrix. In such embodiments, the analysis may use machine learning.

In the example of FIG. 5, the array 131 is split into four zones 132-135. The zones comprise a right zone 132, a left zone 133, a centre zone 134 and a top zone 135. If the device 100 is positioned correctly, the right zone 132 corresponds to the right edge 2 of the bed 10 and areas above the right edge 2 of the bed 10. Similarly, the left zone 133 corresponds to the left edge 3 of the bed 10 and areas above the left edge 3 of the bed 10. The centre zone 134 corresponds to the centre 4 of the bed 10 and the top zone 135 corresponds to the area above the centre 4 of the bed.

The processing unit 150 is operable to determine the proportion of segments in each zone 132-135 that are occupied and compare this proportion to a zone threshold value. If the proportion exceeds the zone threshold value, the zone is determined to be occupied by the bed occupant. If the proportion is below the zone threshold value, the zone is determined to be unoccupied. By determining which zones are occupied and considering the output of the range sensor 140, the processing unit 150 can determine the likely position of the bed occupant 1. Based on the determined position, the processing unit can subsequently determine if a bed exit event is likely or in progress. The processing unit 150 may additionally consider the overall proportion of occupied segments in order to determine whether a determined position is potentially valid.

Typically, given that the zones 132-135 differ in size and since location within particular zones 132-135 can vary the likelihood of bed exit events, the zone threshold values can vary for different zones 132-135. In the present example, the zone threshold values for the right and left zones 132, 133 may be say 12.5, 18.75 or 25%; the zone threshold value for the centre zone 134 may be say 15%; and the zone threshold value for the top zone 135 may be say 1%.

Turning to FIG. 6, some basic examples of this determination are illustrated with respect to the example images 169 wherein occupied segments are white and unoccupied segments are black.

Figure 6A:
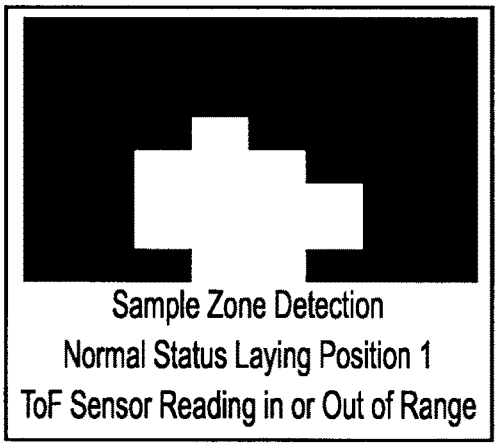
FIG. 6 is a schematic illustration of processed output value matrices so as to indicate both occupied and unoccupied segments in a series of different bed occupancy states.

In FIG. 6a, only the centre zone 134 is occupied. The bed occupant 1 can therefore be determined to be lying in the centre 4 of the bed. Accordingly, a bed exit event is unlikely.

Figure 6B:
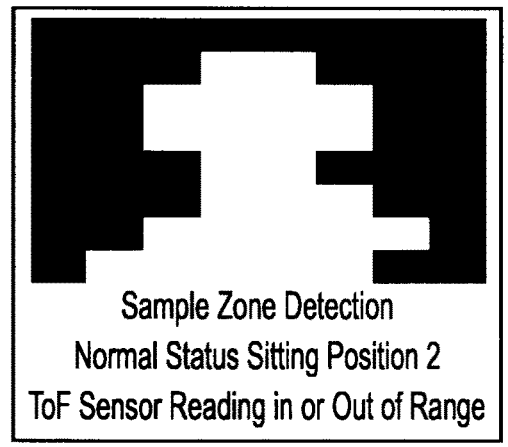

In FIG. 6b, the centre zone 134 and top zone 135 are both occupied. The bed occupant 1 can therefore be determined to be sitting up in the centre 4 of the bed. Accordingly, an imminent bed exit event is unlikely. Nevertheless, this may raise the prospect of a future bed exit event compared to the example of FIG. 6a.

Figure 6C:
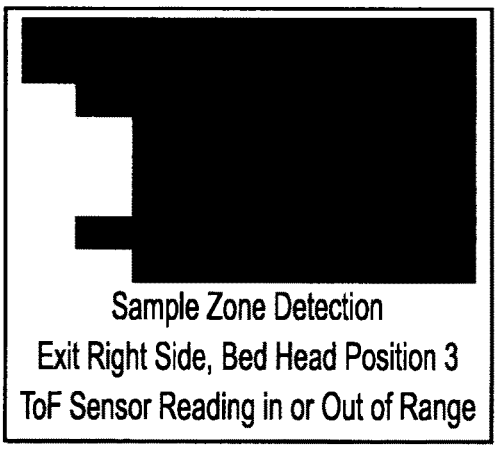

In FIG. 6c, only the right zone 132 is occupied. The bed occupant 1 can therefore be determined to be on the right edge 2. Accordingly, a bed exit event to the right side of the bed is either in progress or imminent. In response to such a determination, the processing unit 150 may output an alarm signal via the communication unit.

Figure 6D:
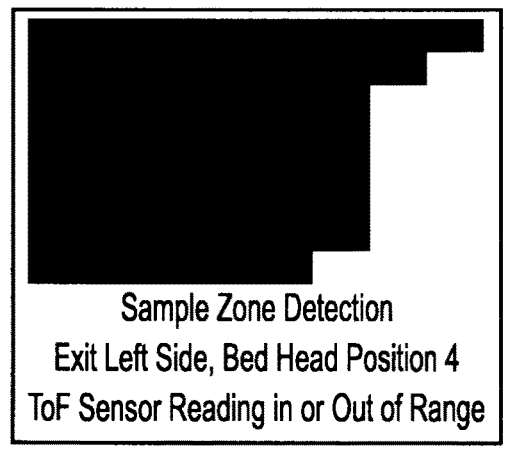

In FIG. 6d, only the left zone 133 is occupied. The bed occupant 1 can therefore be determined to be on the left edge 3 of the bed. Accordingly, a bed exit event to the left side of the bed is either in progress or imminent. In response to such a determination, the processing unit 150 may output an alarm signal via the communication unit.

In some instances, the position of the bed occupant 1 may not be readily resolved. In such cases, the processing unit 150 may also consider the proportion of occupied segments overall and/or the output of range sensor 140.

Figure 6E:
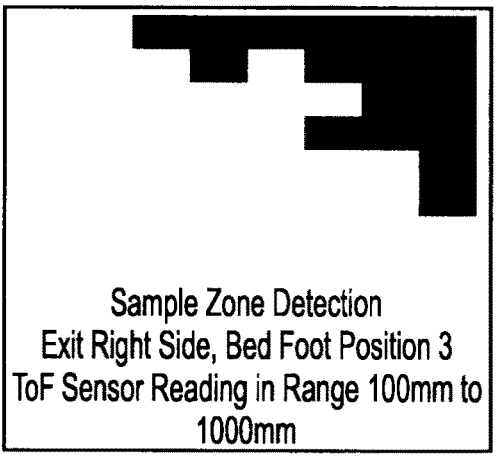

In FIG. 6e, the right zone 132, centre zone 134 and top zone 135 are all occupied. Additionally, the range sensor 140 indicates that there is an object in the range 100-1000 mm from the device 100. The bed occupant 1 can therefore be determined to be on the right edge 2 of the bed and relatively close to the foot board 11. Accordingly, a bed exit event to the right side of the bed is either in progress or imminent. In response to such a determination, the processing unit 150 may output an alarm signal via the communication unit.

Figure 6F:
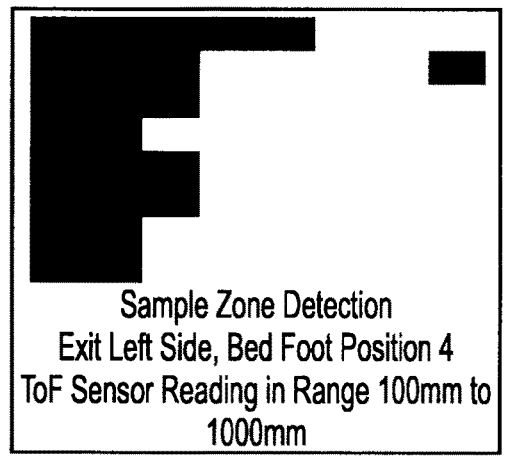

In FIG. 6f, the left zone 133, centre zone 134 and top zone 135 are all occupied. Additionally, the range sensor 140 indicates that there is an object in the range 100-1000 mm from the device 100. The bed occupant can therefore be determined to be on the left edge 3 of the bed and relatively close to the foot board 11. Accordingly, a bed exit event to the left side of the bed is either in progress or imminent. In response to such a determination, the processing unit 150 may output an alarm signal via the communication unit.

Figure 6G:
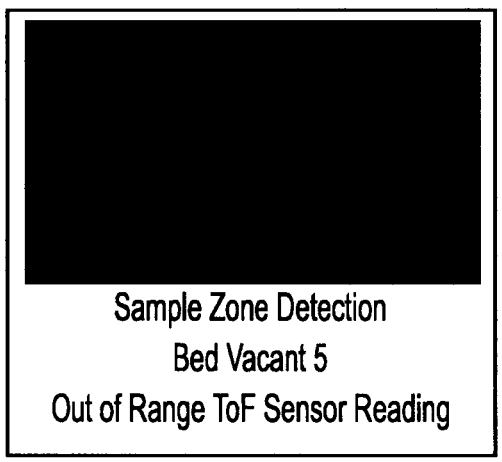

In FIG. 6g, no zones are occupied and no segments are occupied. Additionally, the range sensor 140 indicates that no objects are within detection range. Accordingly, the bed 10 may be determined to be vacant.

Figure 6H:
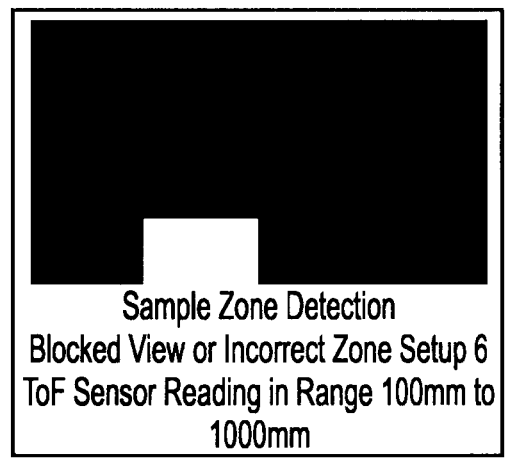

In FIG. 6h, no zones are occupied and but some segments are occupied.

Additionally, the range sensor 140 indicates that that there is an object in the range 100-1000 mm from the device 100. Accordingly, the device 100 may determine that the view is blocked and may output a signal to this effect.

Figure 6I:
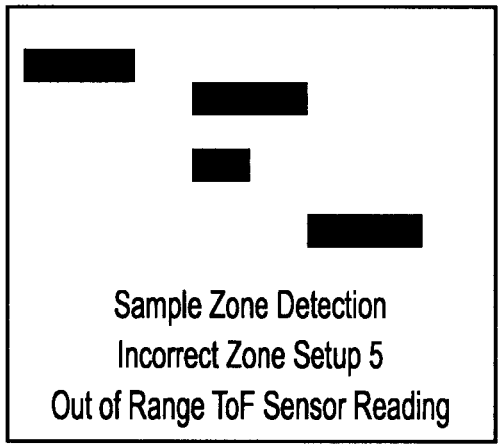

In FIG. 6i, all zones are occupied. Additionally, the range sensor 140 indicates that no objects are within detection range. Accordingly, the device 100 may determine that the device is not positioned or configured correctly and may output a signal to this effect.

Figure 6J:
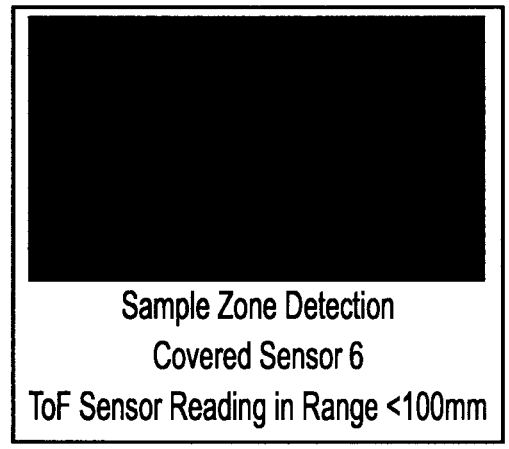

In FIG. 6j, all zones are unoccupied. Additionally, the range sensor 140 indicates that that there is an object within 100 mm of the device 100. Accordingly, the device 100 may determine that the view is blocked and may output a signal to this effect. Similarly, if the range sensor 140 indicates that there is an object within 100 mm of the device 100 and the zones are occupied in accordance with any of FIGS. 6a-6d, the device 100 may also determine that the view is blocked and may output a signal to this effect.

Figure 6K:
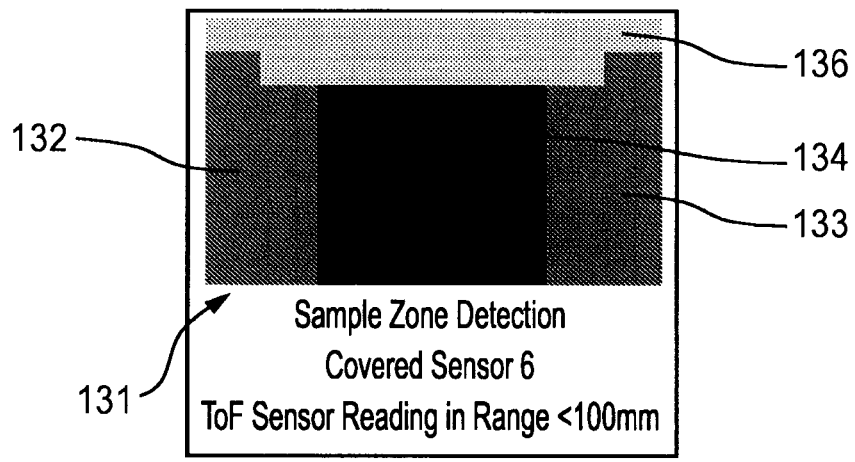

In some embodiments, some of the segments may be assigned to a disabled zone. The processing unit 150 will not consider the output of the segments in the disabled zone. This can be particularly useful if there are additional heat sources close to the bed, such as a portable heater, or if areas outside the bed zone are within the detection area of the sensor 130. An example of an array 131 comprising a disabled zone 136 is illustrated in FIG. 6k. In this example, the disabled zone 136 is at the upper edge of the array 131, similar to the top zone 135 in the previous example but with greater lateral extent and a stepped boundary 137 on each edge. Such a disabled zone 136 omits from processing areas outside the bed 10 when the sensor 130 is mounted on a privacy rail 11.

Figure 7:
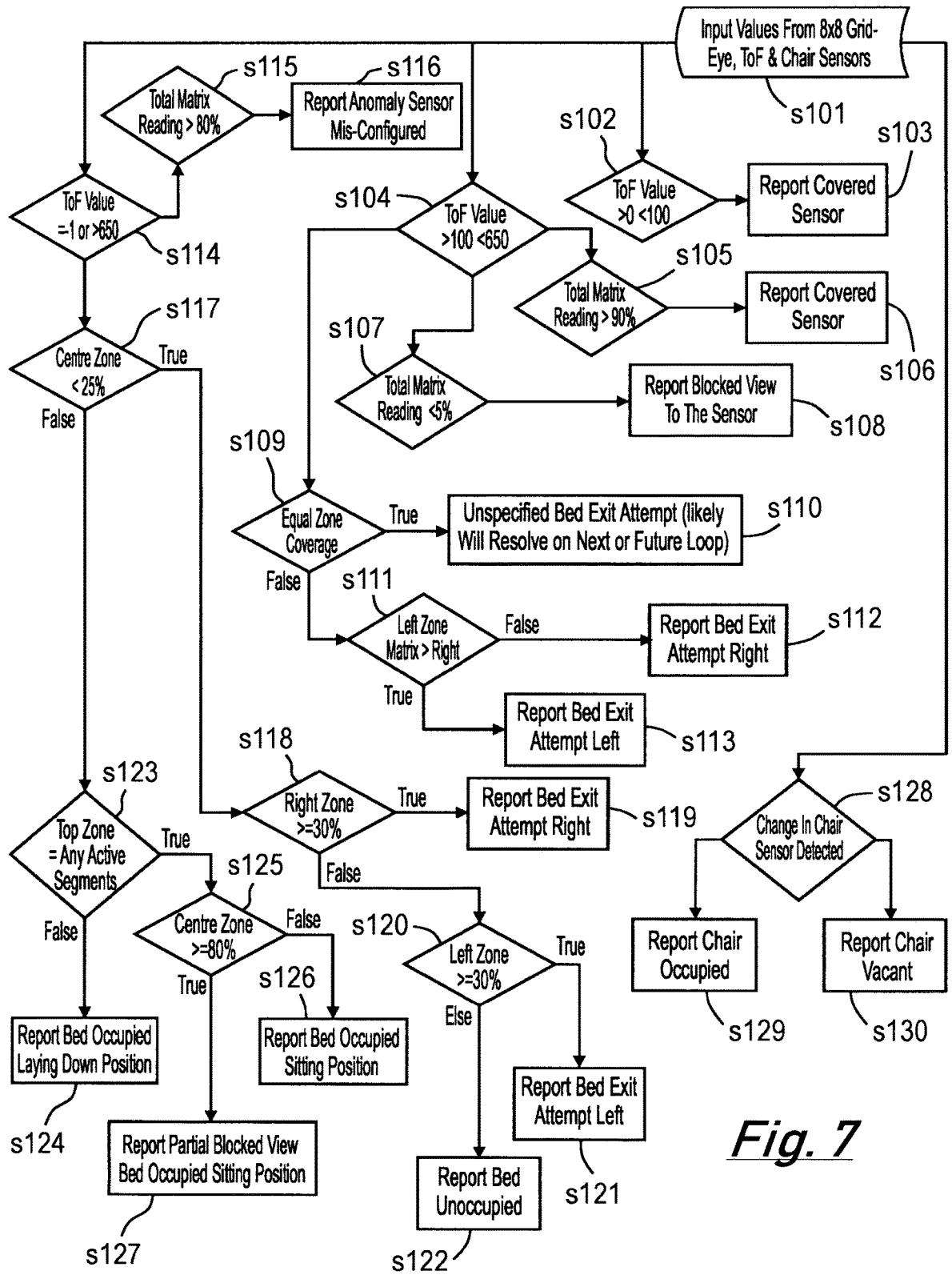
FIG. 7 is a flow chart illustrating one implementation of a bed exit detection method.

An example of an algorithm by which processing unit 150 may make such determinations is illustrated in FIG. 7. At s101 output values from the thermographic sensor 130 and range sensor 140 are received and processed so as to determine the occupied segments, occupied zones and whether any object is present within the detection range of the range sensor 140.

If the range value is less than a minimum at s102, the device 100 may be determined to be blocked and a signal to this effect may be output at s103.

If the range value is within the detection range of the device at s104, the total proportion of occupied segments is considered. If at s105 the occupied segment proportion is greater than 90% the device 100 may be determined to be blocked and a signal to this effect may be output at s106. If at s107 the occupied segment proportion is less than 5% the device 100 may be determined to be blocked and a signal to this effect may be output at s108.

If the total proportion of occupied segments is between 5% and 90%, the relative proportion of occupied segments in each zone is considered at s109. If the relative proportions are not clearly greater to either side, the occupant position may be determined to be unresolved at s110. The process may then revert to s101.

If the relative proportions are clearly to either side at s111, the occupant position may be determined to be a bed exit risk to either side at s112 and s113. An alarm signal to this effect may be output.

If the range sensor 140 indicates that no objects have been detected in the detection range at s114, the total proportion of occupied segments is considered. If at s115 the occupied segment proportion is greater than 80% the device 100 may be determined to be misconfigured and a signal to this effect may be output.

If at s117 it is determined that the proportion of occupied segments in the centre zone 134 is less than 25%, then the proportion of occupied segments in the right zone 132 is considered s118. If this proportion is equal to or exceeds 30%, the occupant position may be determined to be a bed exit risk to the right side at s119. An alarm signal to this effect may be output.

If the proportion of occupied segments in the right zone 132 is less than 30%, then the proportion of occupied segments in the left zone 133 is considered at s120. If this proportion is equal to or exceeds 30%, the occupant position may be determined to be a bed exit risk to the left side at s121. An alarm signal to this effect may be output.

If the proportion of occupied segments in the left zone 133 is also less than 30%, then the bed may be determined to be unoccupied at s 122. A signal to this effect may be output.

In embodiments where the top zone 135 is in operation, if at s117 it is determined that the proportion of occupied segments in the centre zone 134 is greater than 25%, then the existence of occupied segments in the top zone 135 is considered at s123. If there are no occupied segments in the top zone 135, then the occupant position may be determined to be lying in the centre of the bed at s124. A signal to this effect may be output.

If at s123 there are no occupied segments in the top zone 135 then the relative proportion of occupied segments in the top zone 135 is considered at s125. If the proportion of occupied segments is less than 80%, then at step s126 the occupant may be determined to be sitting position. A signal to this effect may be output. Alternatively, if the proportion of occupied segments is greater than or equal to 80%, then at step s127 the occupant may be determined to be sitting position and partially blocking the device view. A signal to this effect may be output.

In embodiments having a disabled zone 136 in place of a top zone 135, s123 and s124 are omitted. Instead, the method proceeds directly from s117 to s125.

Figure 8:
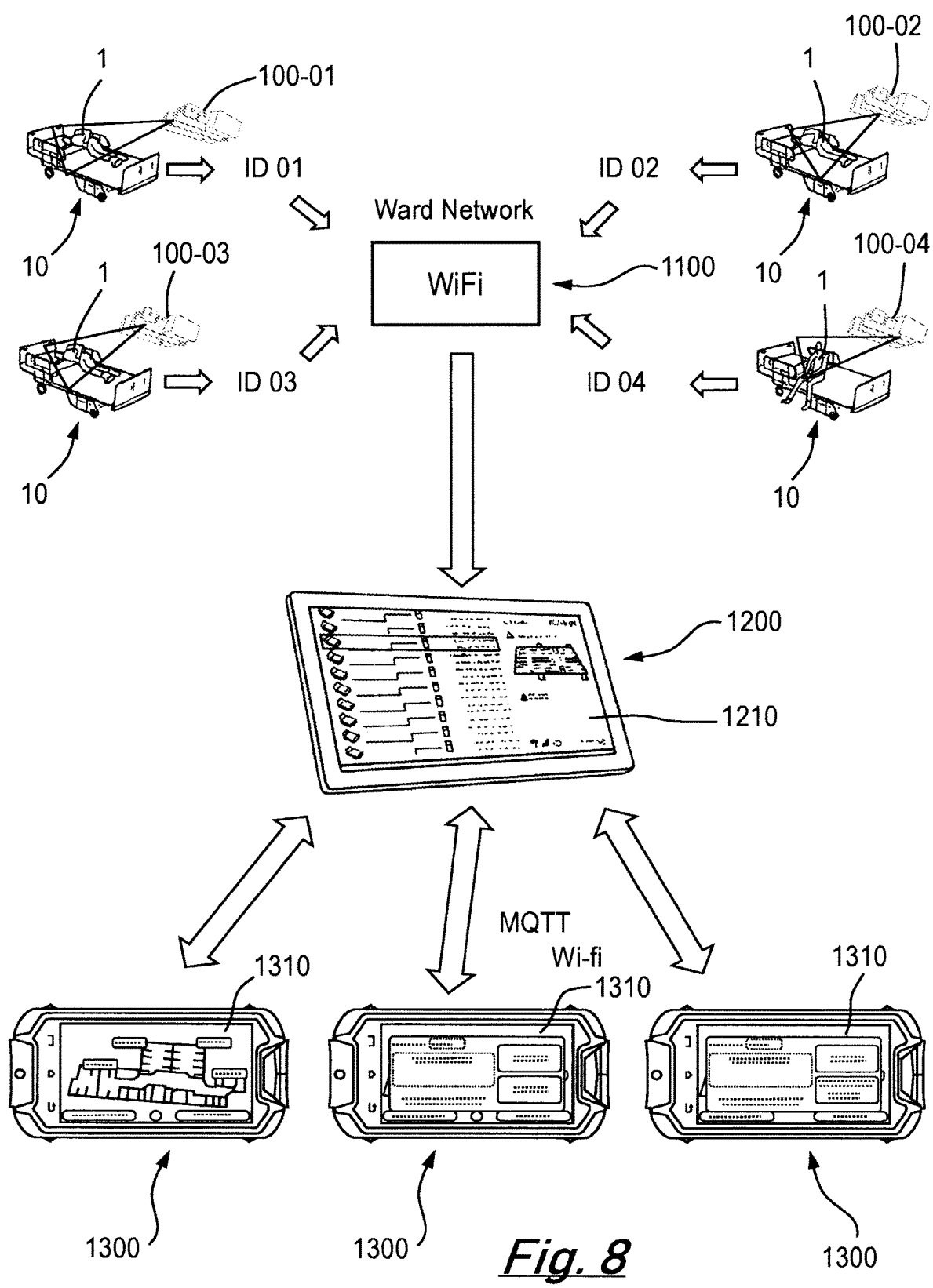
FIG. 8 is a schematic illustration of a system for monitoring multiple bed exit monitoring devices.

In optional embodiments, as shown in FIG. 7, a chair pressure sensor may also be in communication with device 100 via communication unit 180. In such cases, the processing unit 150 may also be operable to determine if there is a change in the output of the chair pressure sensor at s128. Depending on the nature of the change in output of the chair pressure sensor, the chair can either be determined to be occupied at s129 or unoccupied at s130. A signal to this effect may be output. In use, multiple devices 100 (100-01 to 100-04) may be fitted to multiple beds 1, say within a hospital ward or care home, as shown in FIG. 8. The devices 100 may be monitored using a system 1000 comprising a routing hub 1100 which is operable to enable transmission of signals between multiple devices 100 and a control console 1200. The control console 1200 typically comprises a tablet computer. The control console 1200 has a display 1210 operable to display information relating to the current status detected by each device 100, as determined by signals received by the control console 1200.

Figure 9:
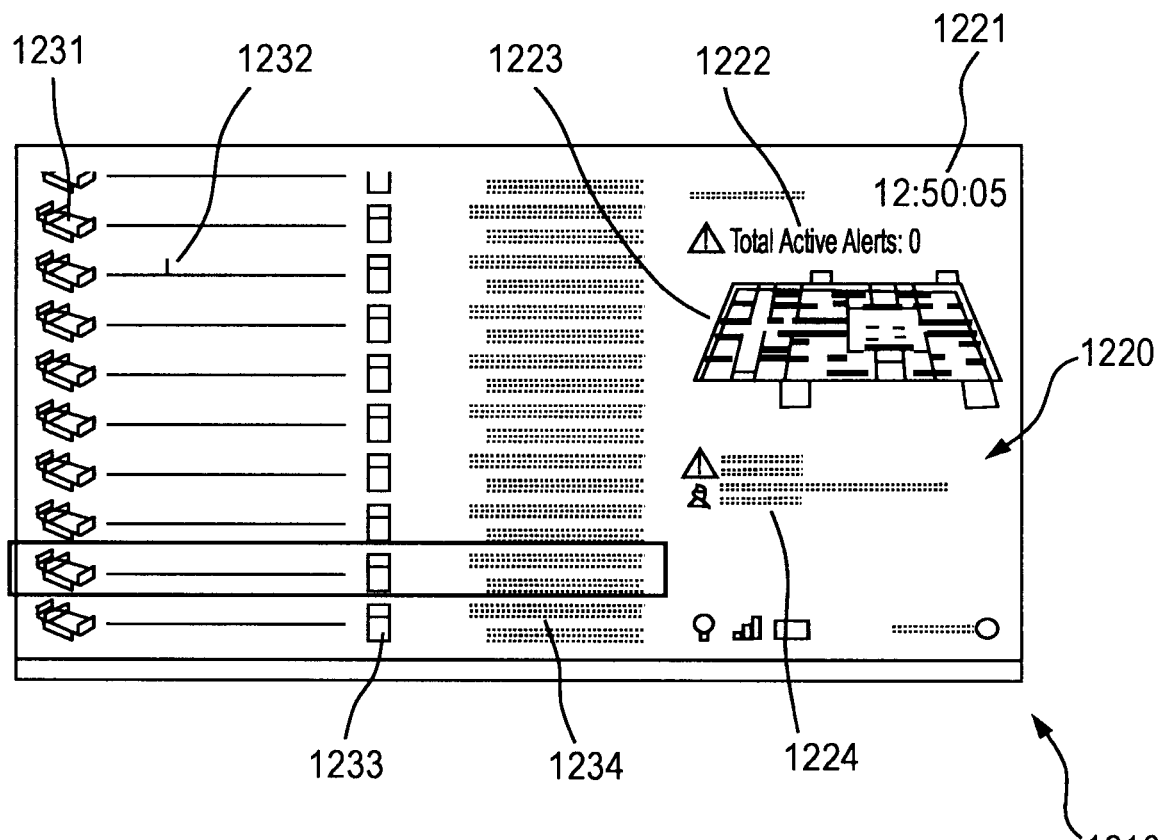
FIG. 9 is a schematic illustration of the display of a control console in the system of FIG. 8.

An enlarged example of display 1210 is shown at FIG. 9. The display 1210 has a first portion 1220 displaying information as to the operation of the system as a whole. This information may include current date and time 1221, number of current bed exit alarms 1222, a map 1223 of the location of beds and a log 1224 of recent status updates. The display has a second portion 1230 containing information about the current status of each device 100. In particular, this may include a status icon 1231, a trace line 1232 indicating recent changes in the output value matrix, a sensor battery heath icon 1233 and bed/patient identity information 1234.

In the event that a bed exit event is detected by one of the devices 100, say device 100-04 in FIG. 8, an alarm signal is output. The alarm signal is received at the control console 1200 and the status information relating to device 100-04 is updated. Additionally, a corresponding alarm signal is output by the control console to one or more carer terminals 1300.

The carer terminals 1300 are provide with at least a display 1310. The carer terminals are typically small tablet computers adapted to be carried by members of the care staff in the ward or care home. Upon receipt of the alarm signal, the carer terminals 1300 output an alarm. Typically, this might include an audio signal and or vibration in addition to information displayed on the display 1310. The display 1310 is operable to display details of the alarm such as the identity of the bed 10, device 100 or bed occupant 1, the location of the bed 10 and the nature of the detected bed exit event. The carer can thus go to the bed 10 and attempt to avert or alleviate the detected bed exit event.

Typically, the carer terminal 1300 is also operable to enable an input to be made in response to an alarm. This can allow a carer to acknowledge receipt of the alarm and/or indicate whether they are responding. This acknowledgment can be transmitted back to the control console 1200. This can enable a record of response activity to be maintained. It may also enable the alert to be cancelled for other carer terminals 1300 once one acknowledgment is received. This can avoid diverting multiple members of staff unnecessarily. Additionally or alternatively, an acknowledgement may be made directly using control console 1200.

In use, as an initial step s1001, each device 100 is set up. This involves mounting the device securely relative to a bed 10, adjusting the sensitivity setting of each device 100, adjusting the allocation of zones to each segment of the thermographic sensor 130 and ensuring each device 100 is in communication with the control console 1200. Additionally, each carer terminal 1300 may also be set up and put in communication with the control console 1200. Subsequently monitoring operation can commence at s1002. This monitoring typically includes each device 100 transmitting status messages to the control console 1200 as required.

In the event that a bed occupant 1 makes a bed exit attempt at s1003, the corresponding device 100 detects the variation in the output value matrix and/or the range sensor output at s1004. The processing unit 150 processes these outputs to determine that a bed exit attempt is in progress at s1005. Consequently, an alarm signal is output to the control console 1200 at s1006.

The alarm signal results in an alarm being output by the control console 1200 at s1007. This alarm can be output on display 1210 at s1008. The alarm is also transmitted to carer terminals 1300 such that these terminals 1300 also output the alarm at s1009. Additionally, details of the alarm may be transmitted to an archive terminal or a supervisor or a computer or mobile device of a supervisor at s1010. If no acknowledgement is made using carer terminals 1300 or control console 1200 then this lack of action is communicated to the archive terminal, supervisor or computer/mobile device of the supervisor at s1011.

If an acknowledgment is made at s1012, the control console 1200 can output the acknowledgement at s1013 and the acknowledgement can be communicated to the archive terminal, supervisor or computer/mobile device of the supervisor at s1014. The carer who made the acknowledgement at s1012 can then attend to the bed occupant at s1015. Assuming timely response on the part of the carer, this can result in the bed exit attempt being resolved at s1016. Monitoring can then resume at s1002.

The one or more embodiments are described above by way of example only. Many variations are possible without departing from the scope of protection afforded by the appended claims.

The invention claimed is:

1. A bed exit detection device comprising: a thermographic sensor comprising an array of sensing elements, each sensing element, from the array of sensing element, operable to output signals corresponding to a temperature of a corresponding segment within a field of view of the thermographic sensor and to generate an output value matrix from the output signals of each individual sensing element, from the array of sensing elements; a range sensor operable to determine and output a distance between the range sensor and an object; and a processing unit operable to process the output value matrix of the thermographic sensor and the distance output by the range sensor so as to determine a position of a bed occupant and determine a likelihood of a bed exit event based on the position of the bed occupant, wherein the processing unit is operable to determine whether each output value in the output value matrix is within a characteristic range and if so to identify the corresponding segment as an occupied segment, wherein an upper threshold of the characteristic range is pre-set and wherein a lower threshold of the characteristic range is varied in response to i) an overall output of the thermographic sensor and to a sensitivity setting of the thermographic sensor or ii) the sensitivity setting of the thermographic sensor.

2. The bed exit detection device as claimed in claim 1, wherein the range sensor is operable to determine a distance between the range sensor and any object within a predetermined maximum distance of the range sensor, the predetermined maximum distance being less than a length of a bed containing the occupant.

3. The bed exit detection device as claimed in claim 1, wherein the bed exit detection device is provided with a communication unit operable to transmit data to or receive data from one or more external devices, said data including status signals and/or an alarm signal when the bed exit event is detected.

4. The bed exit detection device as claimed in claim 1, wherein the processing unit is operable to divide the output value matrix into a plurality of zones, each zone defined by to reference to a subset of segments.

5. The bed exit detection device as claimed in claim 4, wherein the processing unit is operable to determine whether each zone is occupied by determining whether a number of occupied segments within a zone exceeds a zone threshold value.

6. The bed exit detection device as claimed in claim 5, wherein the processing unit is operable to determine a position of a bed occupant by reference to occupied zones.

7. The bed exit detection device as claimed in claim 1, wherein the processing unit is operable to monitor an overall proportion of occupied segments and/or an output of the range sensor.

8. The bed exit detection device as claimed in claim 1, wherein the bed exit detection device is mounted in an elevated position with respect to the bed to be monitored.

9. The bed exit detection device as claimed in claim 1, wherein the bed exit detection device comprises an illumination unit provided alongside the thermographic sensor and the range sensor.

10. A method of operating a bed exit detection device comprising: a thermographic sensor of a type comprising an array of sensing elements, each sensing element, from the array of sensing elements, operable to output signals corresponding to a temperature of a corresponding segment within a field of view of the thermographic sensor and to generate an output value matrix from the output signals of each individual sensing element, from the array of sensing elements; and a range sensor operable to determine and output a distance between the range sensor and an object, the method comprising steps of: processing the output value matrix of the thermographic sensor and the distance output by the range sensor so as to determine a position of a bed occupant and determine a likelihood of a bed exit event based on the position of the bed occupant; wherein the processing unit is operable to determine whether the each output value within the output value matrix is within a characteristic range and if so to identify no corresponding segment as an occupied segment, wherein an upper threshold of the characteristic range is pre-set and wherein a lower threshold of the characteristic range is varied in response to i) an overall output of the thermographic sensor and to a sensitivity setting of the thermographic sensor or ii) the sensitivity setting of the thermographic sensor.

11. The method as claimed in claim 10, wherein the method includes using the range sensor to determine the distance to objects within a predetermined maximum distance of the range sensor, the predetermined maximum distance being less than a length of the bed containing the occupant.

12. The method as claimed in claim 10, wherein the method includes transmitting data to or receiving data from one or more external devices, the data including status signals and/or an alarm signal when the bed exit event is detected.

13. The method as claimed in claim 10, wherein the sensitivity setting is selected by outputting an image representative of the output value matrix for a bed to be monitored containing an occupant; reducing the sensitivity setting of the thermographic sensor until substantially no features are detectable in the image representative of the output value matrix image; and then increasing the sensitivity setting of the thermographic sensor until features corresponding to the position of the occupant on the bed are visible in the image representative of the output value matrix.

14. The method as claimed in claim 10, wherein the output value matrix is divided into a plurality of zones, each zone defined by reference to a subset of segments.

15. The method as claimed in claim 14, wherein the method includes determining whether each zone is occupied by determining whether a number of occupied segments within a zone exceeds a zone threshold value.

16. The method as claimed in claim 15, wherein the method includes determining the position of a bed occupant by reference to occupied zones.

17. The method as claimed in claim 10, wherein the method includes monitoring an overall proportion of occupied segments and/or an output of the range sensor.

18. The method as claimed in claim 10, wherein the output value matrix comprises a disabled zone, an output of segments in the disabled zone being excluded from processing.

19. A bed exit monitoring system for monitoring multiple beds, the bed exit monitoring system comprising: one or more bed exit detection devices provided for each monitored bed, from the multiple beds, each of the one or more bed exit detection devices comprising: a thermographic sensor comprising an array of sensing elements, each sensing element, from the array of sensing elements, operable to output signals corresponding to a temperature of a corresponding segment within a field of view of the thermographic sensor and to generate an output value matrix from the output signals of each individual sensing element, from the array of sensing elements; a range sensor operable to determine and output a distance between the range sensor and an object; and a processing unit operable to process the output value matrix of the thermographic sensor and the distance output by the range sensor so as to determine a position of a bed occupant and determine a likelihood of a bed exit event based on the position of the bed occupant; a control console in communication with each bed exit detection device and operable to output a status indication in response to signals received from each bed exit detection device; wherein the processing unit is operable to determine whether each output value in the output value matrix is within a characteristic range and if so to identify the corresponding segment as an occupied segment, wherein an upper threshold of the characteristic range is pre-set, and wherein a lower threshold of the characteristic range is varied in response to i) an overall output of the thermographic sensor and to a sensitivity setting of the thermographic sensor or ii) the sensitivity setting of the thermographic sensor.

20. The bed exit monitoring system as claimed in claim 19, wherein the system further comprises one or more carer terminals in communication with the control console.

21. The bed exit monitoring system as claimed in claim 20, wherein in response to an alarm signal generated by the bed exit detection device, the control console is operable to communicate the alarm signal to each carer terminal.

22. The bed exit monitoring system as claimed in claim 21, wherein in response to an alarm signal, each carer terminal is operable to output an alarm.

23. The bed exit monitoring system as claimed in cam 22, wherein each carer terminal is operable to generate an acknowledgement signal for an alarm in response to activation of user input means.

24. The bed exit monitoring system as claimed in claim 19, wherein the control console is operable to output any one or more of: an alarm in response to an alarm signal generated by a bed exit detection device; status information relating to each bed exit detection device; or information relating to any acknowledgement signals received.

* * * * *